United States Patent
Machida

(10) Patent No.: US 7,110,805 B2
(45) Date of Patent: Sep. 19, 2006

(54) MAGNETIC RESONANCE IMAGING FOR A PLURALITY OF SELECTIVE REGIONS SET TO OBJECT CONTINUOUSLY MOVED

(75) Inventor: Yoshio Machida, Nasu-Gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 470 days.

(21) Appl. No.: 09/957,461

(22) Filed: Sep. 21, 2001

(65) Prior Publication Data

US 2002/0115929 A1    Aug. 22, 2002

(30) Foreign Application Priority Data

Sep. 25, 2000 (JP) ............................. 2000/291115

(51) Int. Cl.
*A61B 5/55* (2006.01)
(52) U.S. Cl. ...................... 600/415; 600/410
(58) Field of Classification Search ............... 600/410, 600/415; 324/307, 309
See application file for complete search history.

(56) References Cited

U.S. PATENT DOCUMENTS

| | | | |
|---|---|---|---|
| 5,111,144 A | | 5/1992 | Kuhn |
| 5,327,088 A | * | 7/1994 | Pipe ........................... 324/309 |
| 5,378,986 A | * | 1/1995 | Seo et al. .................... 324/309 |
| 5,423,315 A | * | 6/1995 | Margosian et al. ......... 600/410 |
| 5,498,961 A | | 3/1996 | Kuhn et al. |
| 5,636,636 A | * | 6/1997 | Kuhn et al. .................. 600/415 |
| 5,969,525 A | | 10/1999 | Van Driel et al. |
| 6,385,478 B1 | * | 5/2002 | Hajnal ......................... 600/410 |
| 6,483,305 B1 | * | 11/2002 | Miyamoto ................... 324/307 |

OTHER PUBLICATIONS

Herlihy et al, "Continuous Scanning Using Single Shot Fast Spin Echo on a Short Bore Neonatal Scanner", Proc. ISMRM '98, p. 1942.

Machida et al, "Velocity Independent Phase-Shift Stabilization (VIPS) Technique in FSE Flow Imaging", Proc. Intl. Soc. Magn. Reson. Med. 7 (1999), p. 1910.

Japanese Patent Publication Laid-opn (Unexamined) No. 8-71056 published on Mar. 19, 1996, filed on Sep. 5, 1994, applicant: Kabushiki Kaisha Toshiba, and inventor: H. Kanazawa—partial translation.

* cited by examiner

*Primary Examiner*—Brian L. Casler
*Assistant Examiner*—Julianne M. Sullivan
(74) *Attorney, Agent, or Firm*—Nixon & Vanderhye P.C.

(57) ABSTRACT

MRI echo data is acquired by performing selective-excitation on regions composed of multi-slices of an object, while the object is moved continuously. The positions of the multi-slices are moved within a predetermined imaging range fixedly determined by an MRI system, according to object movement. This allows positions of the multi-slices to be changed in compliance with the moved object, so that the multi-slices positionally track with the object within the imaging range. Accordingly, a multi-slice imaging technique can be provided, which is executable during even continuous movement of the object.

23 Claims, 7 Drawing Sheets

MULTI-SLICE IMAGING WITH TABLETOP MOVED
(NUMBER OF MULTI-SLICES = 3)

MULTI-SLICE IMAGING WITH TABLETOP MOVED
(NUMBER OF MULTI-SLICES = 3)

MULTI-SLICE IMAGING WITH TABLETOP MOVED
(USING PRE-SATURATION PULSE)

MAGNETIC RESONANCE IMAGING FOR A PLURALITY OF SELECTIVE REGIONS SET TO OBJECT CONTINUOUSLY MOVED

BACKGROUND OF THE INVENTION

1. Technical Field

The present invention relates to a magnetic resonance imaging (MRI) system for medical use, and in particular, to a magnetic resonance imaging system capable of imaging a plurality of selective regions, such as multi-slice regions, while an object to be imaged is continuously moved in a certain direction.

2. Related Art

In general, magnetic resonance imaging (MRI) can be defined as the imaging technique that magnetically excites nuclear spins of an object placed in a static magnetic field with a radio-frequency signal at a Larmor frequency and reconstructs an image from MR signals generated due to the excitation.

Recently, in the field of the magnetic resonance imaging, there has been proposed a technique for imaging an object laid on a tabletop moved continuously in its longitudinal direction, in order to obtain an image whose field of view is wider than a system's own fixed imaging range. For instance, the "imaging range" is composed of a slice of several centimeters in thickness, and the "wider imaging range" than the fixed imaging range is composed of a region of some 40 centimeters assigned to the abdomen of an object.

A magnetic resonance imaging system based on a fundamental technique directed to such imaging is equipped with a radio-frequency oscillator. This oscillator is used to adjust the carrier frequency of a radio-frequency excitation pulse for selective excitation, depending on a slice-directional position of a specified section (single slice) to be imaged of an object, in cases where imaging is carried out while the object is moved.

Concretely, when a central frequency corresponding to magnetic intensity created by a magnetic resonance imaging system and a carrier frequency of an RF pulse to be applied to an object P is $f_0 + \Delta f$, $\Delta f$ is adjusted depending on a movement of the object P. One example is to acquire an axial image while the tabletop of a patient couch is moved. To perform such imaging, the adjustable frequency $\Delta f$ is given by a formula of $$\Delta f = (\gamma \cdot G_s \cdot V \cdot TR)/2\pi \text{ [Hz]},$$

in which $\gamma$ is a gyromagnetic ratio, $G_s$ is a magnitude of strength of a slice-directional gradient pulse [T/m], V is a moving speed of the tabletop [m/s], and TR is a repetition time [s].

This way of adjustment enables the position of a selectively excited slice to track a desired particular section in a continuous manner during a movement of the object. This will lead to an improved throughput, because the imaging can be done with the object moved.

The above imaging technique is also provided by another example, which is shown by the paper "A H Herlihy et al., "Continuous scanning using single shot fast spin echo on a short bore neonatal scanner," ISMRM '98, p. 1942. This paper provides a continuous imaging technique through the control of the carrier frequency for selective excitation in connection with movement of a tabletop in performing a single shot FSE sequence.

The carrier frequency for the single shot FSE sequence is controlled on the following formula of $$\Delta f_k = \Delta f_0 + (\gamma \cdot G_s \cdot V \cdot ETS^*(k+\tfrac{1}{2}))/2\pi \text{ [Hz]},$$

in which $\Delta f_0$ is an offset amount of the carrier frequency of the first excitation pulse, $\Delta f_k$ ($\geq 1$) is an offset amount of the carrier frequency of the k-th refocusing pulse, and ETS is an echo spacing [s].

The foregoing conventional MR imaging involving a continuous movement of an object (actually a tabletop) shows single slice imaging or sequential multi-slice imaging, which is carried out in a state where a moving direction of an object is made to agree with a direction of a slice selection axis. However, conventional MR imaging does not show the way of multi-slice imaging involving simultaneous selective-excitation of a plurality of slices. In addition, there have been no teachings about oblique imaging of multiple slices, which is one modification from multi-slice imaging, in which a slice selection axis is obliquely set to a moving direction of an object. As understood from the above, the conventional MR imaging that involves a continuous movement of an object is short of various imaging modes that will be frequently required in actual diagnosis. Thus this leads to the problem that it is difficult to perform speedy imaging, because data cannot be acquired with efficiency.

Furthermore, conventional MR imaging that involves a continuous movement of an object does not provide practical ways to reduce artifacts, which will normally be caused due to constant-speed movements of the tabletop (that is, an object).

SUMMARY OF THE INVENTION

The present invention has been made with due consideration to the foregoing drawbacks of conventional MR imaging that involves a continuous movement of an object. An object of the present invention is to make it possible that the MR imaging that involves a continuous movement of an object is able to employ imaging techniques and image-quality improving techniques, such as multi-slice imaging (including oblique imaging of multiple slices) and suppression of artifacts resulting from movement of an object, all of which are greatly effective in actual medical treatment.

In order to accomplish this object, a magnetic resonance imaging system according to an exemplary embodiment of the present invention comprises scanning means for selectively exciting in turn a plurality of regions of an object acquiring echo data from the object while the object is continuously moved; and processing means for producing image data from the echo data acquired by the scanning means. The scanning means includes position-moving means for moving the plurality of selectively excited regions according to a movement of the object such that the plurality of regions are selectively excited in sequence region by region within a predetermined imaging range.

Preferably, the imaging range is determined fixedly in space by the magnetic resonance imaging system. Still preferably, the plurality of regions are composed of multi-slices of the object. Still, a slice-selective axis given to the multi-slices may be made to agree with a moving direction of the object, or may be made to be different from the moving direction of the object.

It is also preferred that the scanning means includes means for adding another slice to a tail of the multi-slices as a slice belonging to the plurality of multi-slices in the moving direction, in cases where a head slice of the multi-slices in the moving direction goes beyond the imaging range.

These configurations are able to provide multi-slice imaging performed with an object moved continuously, which is helpful in actual medical treatment and is able to acquire data in improved efficiency. It is possible to obliquely set a slice-selective axis of multi-slices to a moving direction of an object. Hence, oblique imaging of multi-slices, which is modified from the multi-slice imaging, can be done. The imaging involving an object's continuous movement can therefore be enhanced in its functions, providing the system with improved convenience.

Further, even if an MRI system provides only a narrow imaging range as a "range that can be imaged (photographable range)," a region to be examined having a "wider range" than the narrow range can be imaged and a patient's throughput can be improved.

When the magnetic resonance imaging system is shortened in its bore axis in consideration of compactness, it is natural that an FOV (field of view) becomes smaller than that obtained by a longer bore type of system. Even in such a case, the present invention can be employed, ensuring a wider FOV than a "region that can be imaged."

The magnetic resonance imaging method according to the present invention is configured to have the same principle as the above, providing the above-mentioned functions and advantages as well.

In addition, the magnetic resonance imaging system according to the present invention may be configured in such a manner that, in the foregoing configurations, echo data that have been acquired are subject to their phase correction. This prevents or suppresses artifacts from being caused due to phase shifts of signals in slices resulting from object's movements. It is also possible to include a preparation pulse in a pulse sequence used for scanning, which is helpful in preferable suppression of unnecessary signals and others.

Further, usable is a pulse sequence having a gradient pulse to be applied in the moving direction of the object, in which a phase compensation pulse for nulling a gradient moment of a first or second order is added to at least part of the gradient pulse. This addition of the phase compensation pulse is effective for compensating disturbances in signal phases resultant from object's movements, so that artifacts on account of the phase disturbances can be prevented or suppressed.

Still further, a pulse sequence can be configured by a train of pulses, which is formed on a fast spin echo method, of which gradient to be applied in a moving direction of an object meets, at least partly, a VIPS condition. This is effective for compensating disturbances in signal phases resultant from object's movements, so that artifacts on account of the phase disturbances can be prevented or suppressed. Additionally, a data acquisition time can be shortened.

DETAILED DESCRIPTION OF THE PREFERRED EMBODIMENTS

Referring to the accompanying drawings, preferred embodiments of the present invention will now be described.

First Embodiment

Figure 1:
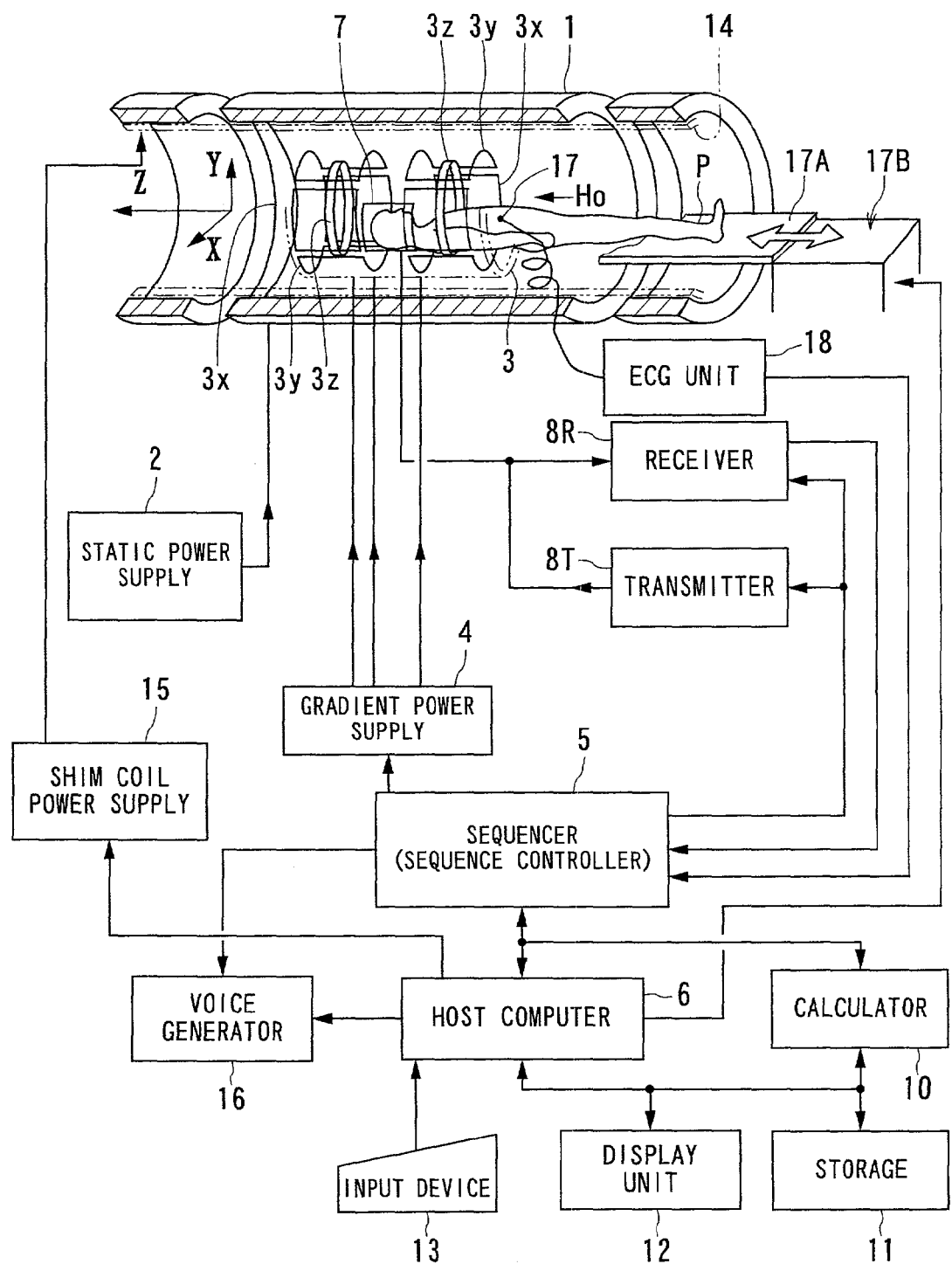
FIG. 1 shows an outlined configuration of a magnetic resonance imaging system according to embodiments of the present invention.

A first embodiment of the present invention will now be described. FIG. 1 shows an outlined configuration of an MRI (magnetic resonance imaging) system used in common in the following various embodiments.

The MRI system comprises a patient couch portion on which an object (patient) P lies down, static magnetic field generating components for generating a static magnetic field, magnetic field gradient generating components used for appending positional information to the static magnetic field, transmitting/receiving components for transmitting and receiving radio-frequency signals, control and arithmetic operation components responsible for both control of the whole system and image reconstruction, and electrocardiographing components for acquiring an ECG signal indicative of cardiac temporal phases of the object P.

The static magnetic field generating components include a magnet 1 formed into, for example, a superconducting type, and a static power supply 2 for supplying a current to the magnet 1. These components are thus able to generate a static magnetic field $H_0$ in an axial direction in a cylindrical bore (diagnostic space) into which an object to be imaged P is inserted. In this embodiment, the axial direction is made to agree with the Z-axis direction of the X-Y-Z orthogonal coordinate system. The magnet is equipped with shim coils 14. A current used to homogenize the static magnetic field is supplied from a shim coil power supply 15 to the shim coils 14 under the control of a host computer described later.

The patient couch portion includes a patient couch 17 having a tabletop 17A at the top. On the tabletop 17A, an object to imaged P is laid on her or his back, for example. The tabletop 17A is retractably moved in its longitudinal direction (i.e., the Z-axis direction) in responses to operations of a not-shown drive mechanism incorporated in the patient couch 17. The drive mechanism is configured to receive a drive command for the host computer later described, so that its drive function is activated in reply to the drive command. When the tabletop 17A is moved in its longitudinal direction as shown in both directions shown in arrows in FIG. 1, the object P laid thereon can also be moved continuously in the Z-direction and retractably inserted in the cylindrical bore of the magnet 1.

The magnetic field gradient generating components includes a gradient coil unit 3 incorporated in the magnet 1. The gradient coil unit 3 includes three pairs (kinds) of x-, y-, and z-coils 3x to 3z used to generate magnetic field gradients changing in strength in the mutually-orthogonal X-axis, Y-axis, and Z-axis directions. The magnetic field gradient generating components further includes a gradient power supply 4 for supplying current to the x-, y-, and z-coils 3x to 3z. The gradient power supply 4 supplies a pulsed current used to generate a magnetic field gradient to the x-, y-, and z-coils 3x to 3z under the control of a sequencer 5 described later.

The pulsed current supplied from the gradient power supply 4 to the x-, y-, and z-coils 3x to 3z is controlled respectively, whereby magnetic field gradients changing in the three axial directions, that is, the X-, Y-, and Z-physical directions are synthesized. Thus, mutually-orthogonal logic directions in which a slice gradient $G_s$, a phase encode gradient $G_e$, and a readout (frequency encode) gradient $G_r$ are applied can be specified and changed arbitrarily. The magnetic field gradients to be applied in the slice direction, phase encode direction, and readout direction are superposed on the static magnetic field $H_0$.

The transmitting/receiving components includes, in addition to an RF coil 7 located in the vicinity of the object P in the scanning space inside the magnet 1, a transmitter 8T and a receiver 8R connected to the coil 7. Both of the transmitter 8T and the receiver 8R operate under the control of a sequencer 5 described later. The transmitter 8T supplies to the RF coil 7 RF current pulses at a Larmor frequency, which causes excitation of nuclear magnetic resonance (NMR). The receiver 8R accepts MR signals (RF signals) that the RF coil 7 has received, carries out various kinds of signal processing on the MR signals, and A/D-converts the MR signals to digital data (original data). The signal processing includes pre-amplification, intermediate-frequency conversion, phase detection, lower-frequency amplification, and filtering.

Furthermore, the control and arithmetic operation components includes a sequencer 5 (often referred to as a sequence controller), a host computer 6, a calculator 10, a storage 11, a display unit 12, and an input device 13. Among them, the host computer 6 has the function of providing the sequencer 5 with information about a pulse sequence and managing the operations of the entire system including the patient couch 17, depending on a variety of modes later described, according to previously installed software programs.

The sequencer 5, which has a CPU and memories, stores pulse sequence information sent from the host computer 6, controls the operations performed by the gradient power supply 4, transmitter 8T, and receiver 8R according to the stored information. In addition, the sequencer 5 temporarily receives digital data corresponding to the MR signals outputted from the receiver 8R, before transferring them to the calculator 10. The pulse sequence information includes all information required for operating the gradient power supply 4, transmitter 8T, and receiver 8R according to a train of pulses composing a pulse sequence. Such information includes information in relation to the strength, duration, and application timing of pulsed currents applied to the x-, y-, and z-coil 3x to 3z.

The host computer 6, sequencer 5, gradient power supply 4, gradient coil unit 3, static magnet 1, transmitter 8T, receiver 8R, and patient couch 17 (tabletop 17A) constitute essentially the scanning means according to one constituent of the present invention. Additionally, the sequencer 5, RF coil 7, and receiver 8R constitute essentially the acquiring means according to another constituent of the present invention.

The calculator 10 receives digital data (original data) sent from the receiver 8R via the sequencer 5, maps the digital data in a Fourier space (known as a k-space or Fourier space) formed by its internal memory, and performs a two-dimensional or three-dimensional Fourier transform with the mapped data so as to reconstruct an image in the real space. Moreover, the controller 10 is also able to carry out such processing as synthesis and difference calculation on the image data.

The storage 11 has a memory and can preserve not only reconstructed image data but also image data that have undergone the synthesis and difference calculation. The storage 11 has a computer-readable recording medium, such as a ROM and a RAM (not shown), into which a pulse sequence used for this MR imaging is recorded in the form of program data.

The display unit 12 is configured to display images. The input device 13 is used by an operator to provide the host computer 6 with desired imaging conditions, a pulse sequence, information about image synthesis and difference calculation, and others.

Furthermore, the electrocardiographing components comprises an ECG sensor 17 attached to a patient body to detect an electric ECG signal and an ECG unit 18 performing various processes including digitization with the detected ECG signal and sending it to both the host computer 6 and the sequencer 5. This enables an appropriate determination of synchronous timing for an ECG-gating (electrocardiographing synchronization) technique, so that in response to the determined synchronization timing, an imaging scan on the ECG-gating technique can be performed to acquire data.

Figure 2:
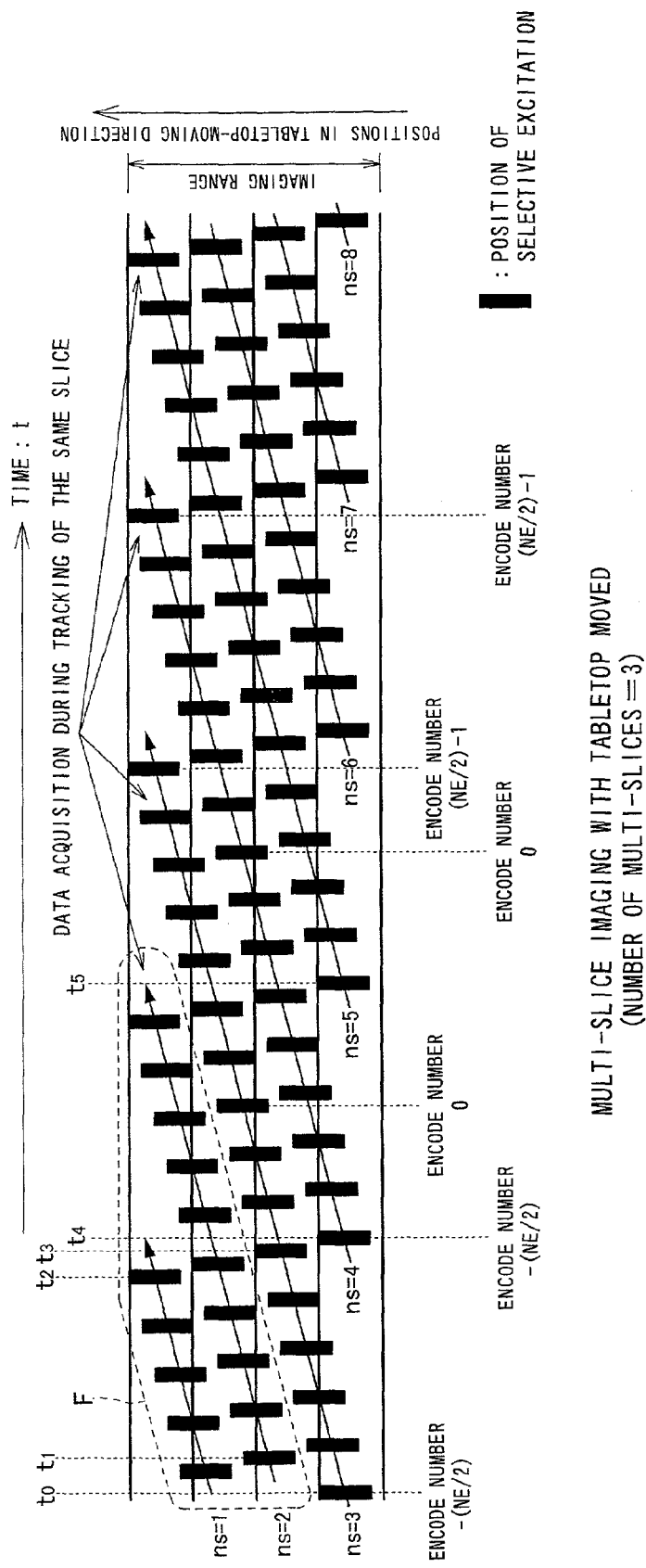
FIG. 2 is an explanation showing multi-slice imaging according to a first embodiment, in terms of the relationship among the time, movement of a tabletop (i.e., object), and selectively excited positions of multi-slices.
Figure 3:
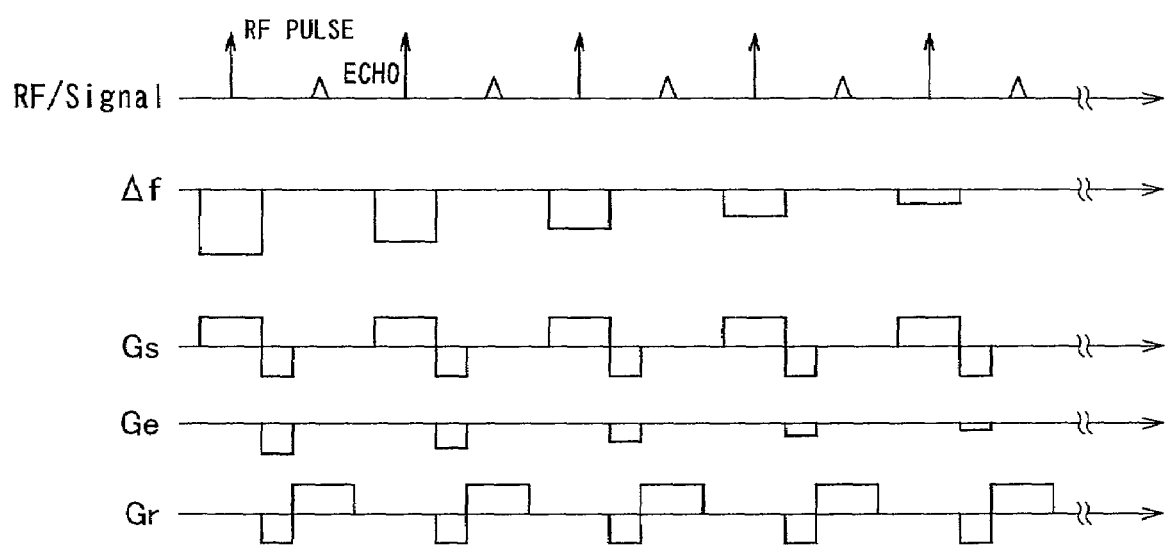
FIG. 3 is a timing chart showing a pulse sequence based on an FE technique adaptable to multi-slice imaging that involves movements of an object.
Figure 4:
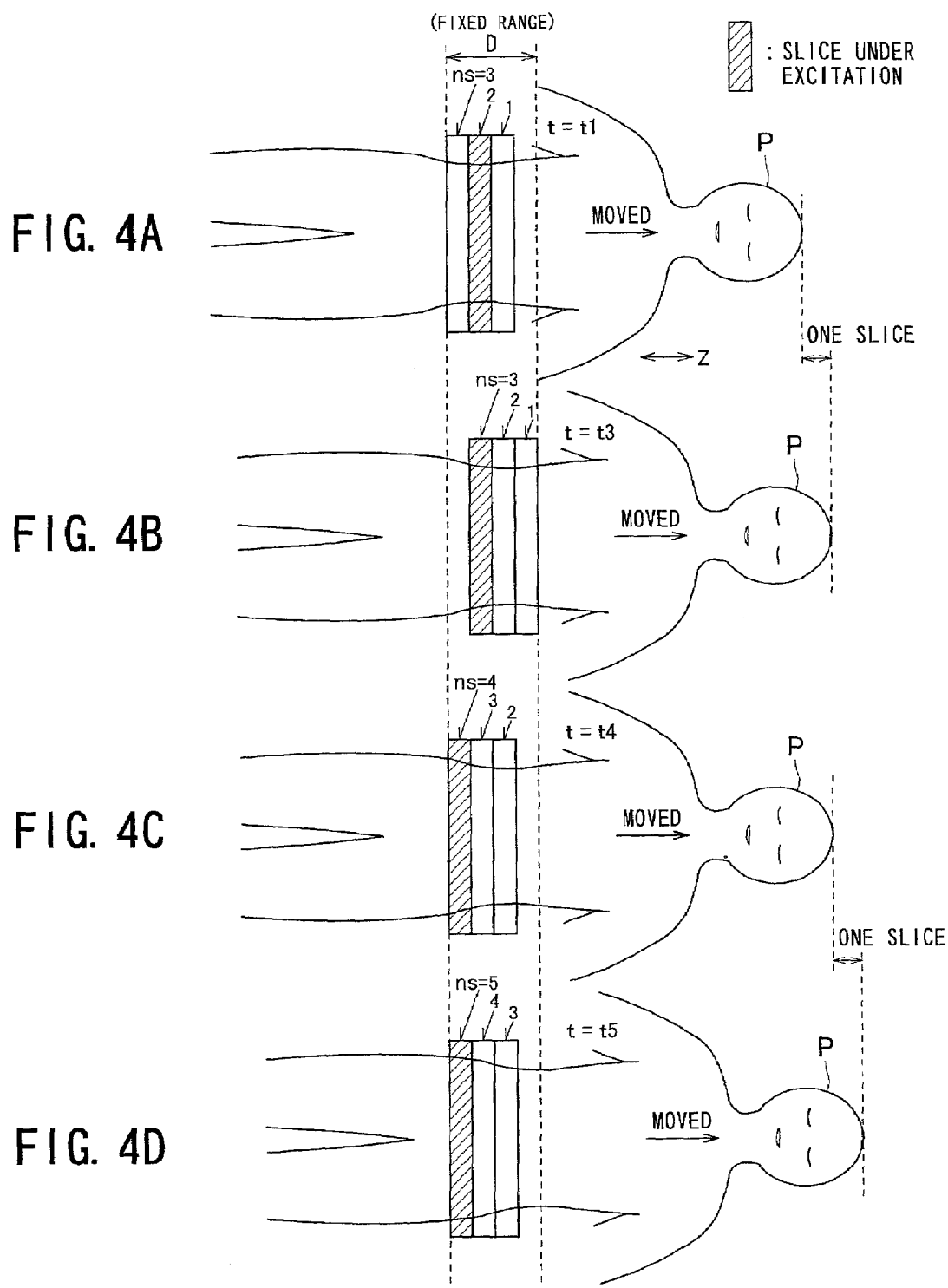
FIGS. 4A to 4D illustrate the relationship among movements of an object, a fixed imaging range, and multi-slice positions according to multi-slice imaging, which are typically shown at several temporal instants taken parameters.

Referring to FIGS. 2 to 4, together with the imaging operations, the principle of the multi-slice imaging executed by the present magnetic resonance imaging system will now be described.

FIG. 2 illustrates the principle of the multi-slice imaging executed in such a manner that the number of multiple slices is set to 3 and the tabletop, that is, an object is continuously moved along its body-axis (Z-axis) direction. This illustration is exemplified by adopting a condition where a moving direction of the object and a slice selecting direction are in agreement with each other.

Data from the multi-slices are acquired on an FE method. A pulse sequence based on the FE (gradient field echo) method, which is applied to each slice, is determined as shown in FIG. 3. Concretely, one time of selective excitation of each slice is responsible for acquisition of a single echo, and such acquisition of each echo is repeated by the number of phase encodes.

Pieces of information in relation to this pulse sequence are handed from the host computer 6 to the sequencer 5. Using the pieces of information, the sequencer 5 commands the gradient power supply 4, transmitter 8T, and receiver 8R to perform scanning on the multi-slice technique that, during an interval from the excitation and data acquisition of each slice, allows the remaining slices to be excited. In parallel with this scanning, the host computer 6 provides the patient couch 17B with a control signal to move the tabletop 17A. Hence, in synchronism with the start timing of this scanning, the tabletop 17A is driven to continuously move at a given speed in the longitudinal direction (i.e., Z-axis direction). As a result, a region to be imaged of an object (for example, the abdomen of a patient) is gradually, but continuously, inserted into the imaging space of the magnet 1. The multi-slice imaging can therefore be executed as the patient P is moved continuously.

In FIG. 2, a direction advancing from the left to the right shows a time axis, whilst a direction going upward corresponds to a moving direction of the tabletop. For the sake of an easier understanding, the number of multiple slices is exemplified as being three. As shown in FIG. 2, tiny rectangles depict positions to be selectively excited; to be specific, each rectangle shows a position at which each spatial position undergoes selective excitation at a given temporal instant.

More specifically, as the object P is moved, a region to be imaged of the object P (for instance, the abdomen) gradually begins to come into an imaging range D fixedly determined by the MRI system. This imaging range D is determined based on the size of a uniform region in the static magnetic field, a spread of sensitivity of the RF coil, and/or some imaging parameters such as a repetition time TR to obtain a desired contrast within a given period of time. Responsively to the start of this movement, the sequencer 5 starts the multi-slice scanning based on the FE method at a given timing (refer to $t=t_0$ in FIG. 2). Thus, a certain slice ns=3 that exists in the imaging range D is selectively excited in consideration of a moved position at that timing. Then, another slice ns=1 which locates every two slices, but still exists in the imaging range D, is selectively excited in consideration of a moved position at that timing. Then, the remaining slice ns=2 that exists in the imaging range D is selectively excited in consideration of a moved position at that timing (refer to $t=t_1$). In response to each time of the above excitation, an echo encoded by each of predetermined phase encode amounts is acquired.

After one time of data acquiring operation toward each slice, as stated above, the selective excitation is returned to the initial slice ns=3 again. However, at this time, the slice ns=3 has been spatially moved from the last spatial position when viewing from the MRI system, because the object is under the continuous movement. In consideration of this new spatial position of the slice ns=3 to the MRI system, an offset amount $\Delta f$ of the carrier frequency of a selective excitation pulse is adjusted. This adjustment is controlled in amount in such a manner that the selective excitation is carried out at any time at the position of the slice ns=3 that tracks a desired predetermined slice fixedly located on the object. It is determined that the tabletop 17A is moved at a specified constant speed, this known speed value is taken into account for controlling the offset amount.

Like this, the other slices ns=2 and ns=1, which already experienced the selective excitation once, are subject to the selective excitation in sequence in the same tracking manner as the above.

Hereafter, the above-stated scans are repeated, during which time, at a time of $t=t_3$, the slice ns=1 located at the head of the multi-slices in the object's moving direction moves to the exit-side last position within the imaging range D, and is subjected to the selective excitation. However, to each of the other slices ns=2 and ns=3, there is still left a room for movement to the exit-sided last position within the imaging range D fixedly determined by the MRI system.

Hence, the head-located slice ns=1 is no longer excited at the next selective excitation timing ($t=t_4$), because it exceeds the imaging range D. Instead, at the time of $t=t_4$, another slice ns=4 that has come newly into an entrance-sided first position within the imaging range D. This scheme is also applied to the other slices. For instance, the selective excitation of the slice ns=2 at the exit-sided last position is followed by another slice ns=5 that is newly selectively excited at the entrance-sided first position ($t=t_5$).

In other words, every time the alternately changed head slice reaches the exit-sided border of the imaging range D, a new slice is added to an initial position located inside the entrance-side border of the imaging range D for data acquisition. To realize this changeover, the imaging parameters and a moving speed of the tabletop are matched to each other, so that a predetermined number of multi-slices are still maintained as a whole.

FIGS. 4A to 4D are pictorial illustrations that exemplify the positional relationship among the fixed imaging range D, the moved object P in the body-axis direction thereof, and the multi-slices to be selective-excited at several timings $t_1$, $t_3$, $t_4$ and $t_5$ shown in FIG. 2, respectively. The number of multiple slices, which are subjected to almost concurrent selective-excitation within the imaging range D, is kept to three. As the object P is moved, the three selectively excited slices track the movement and they are always kept at the fixed positions of the object P within the imaging range D. By contrast, when viewing from the MRI system, the three slices are updated in position so that they are successively moved in the same direction as the moving direction of the tabletop within the imaging range D.

Since the directions showing both the time axis and the moved tabletop are determined as shown in FIG. 2, the arrows, each having a tilt to the right, show that the positions of the selective excitation are always the same within the imaging range when viewing from the object P. That is, the same slices are subjected to data acquisition during tracking the slices. While the slices are tracked from the entrance end to the exit end of the imaging range D, each slice undergoes data acquisition at phase encode amounts of $-NE/2$ to $NE/2$. These phase encode amounts are, however, changed at an arbitrary order, not limited to the ascent or descent order, and a set of data necessary to reconstruct an image are finally acquired. When viewing from the system, all the data are acquired from each of the object's slices that pass the positionally fixed imaging range D with phase encode amounts necessary for each slice changed.

As shown in FIG. 2, the data acquisition of a certain slice adjacent to a slice is launched with a delay of about $TD=TR \cdot NE/MS$ (MS=3 in this embodiment), and then completed with a delay of the time TD. As a result, at all the temporal instants during the scanning, the data acquisition for a total number of slices can be performed, while the multi-slice imaging based on the number of slices MS is still maintained.

As described above, the carrier frequency of the selective excitation pulse applied to each of the multiple is controlled in association with the movement of the tabletop. Hence, with the tabletop moved at a constant speed, MR data can be acquired from a certain region of an object (for instance, a 40 cm region of the abdomen) larger than the imaging region (for instance, a size of 15 cm) determined based on the foregoing reason. Higher efficient data acquisition inherently gained from the MR imaging on the multi-slice imaging can be still utilized. Accordingly, performing the multi-slice imaging during a certain period of time makes it possible that a diagnostic region such as the entire abdomen, which requires a wider view than the predetermined imaging range D, is scanned at a higher speed.

The foregoing MR imaging based on the multi-slice technique carried out during a movement of an object P will now be explained from its quantitative conditions for data acquisition. First, various parameters are defined as below;

MS: the number of multiple slices,
NE: the size of a matrix in a phase encode direction,
TR: a repetition time,
TS (=TR·NE): a scan time (a period of time required to acquire data from each slice),
ns: a serial number of slices (0 to NS, NS>MS),
ne: the numbers of the phase encodes (−NE/2 to NE/2-1),
D a width of an imaging range in an object's moving direction, which is viewed from the system,
SI: an interval between slices (=slice thickness ST+slice gap SG), and
$\Delta f$ (ns, ne): an offset amount of the carrier frequency of a slice selective RF pulse (the slice number and the phase encode number). These parameters are determined so as to realize the relationships of a speed of the tabletop $V=D/TS$ [m/s], and the interval between slices $SI=D/MS$ [m].

Generality would be still maintained, even when it is supposed that the slice center d(n, t) of the n-th slice be defined, with respect to the time t, by $d(n, t)=V·t−n·SI$ [m].

Thus, when a formula of $ns=MS·ns1+ns2$ $(0 \leq ns2 < MS)$ is defined, data acquisition timing T(ns, ne) for each slice and an offset amount $\Delta f$ (ns, ne) of the carrier frequency can be expressed by $T (ns, ne)=TS·ns1+TR·int(NE·ns2/MS)+TR·(ns2/MS)$ [s]

and $\Delta f (ns, ne)=(\gamma·Gs·d(n, T(ns, ne))/2\pi$ [Hz].

In the first formula, int represents an integer part and the last term "TR·(ns2/MS)" about the data acquisition timing T(ns, ne) is placed to distribute the MS-piece multiple slices at equal temporal intervals. Hence, as shown in FIG. 2, the acquisition can be performed such that all the multiple slices are updated almost evenly, slice by slice.

As a maximum NS of the serial numbers of the multi-slices gets sufficiently larger than the number of multi-slices, the tabletop can be moved more continuously. Thus, as a whole, the scanning can be done with higher efficiency.

By the way, as shown in FIG. 2, data from "NS-1" slices at the beginning and end of a series of scans cannot be acquired in a complete multi-slice mode of which normal sliced number is MS. In FIG. 2, a portion F encircled by a dotted line means the data acquisition from the "NS-1" slices at the beginning of the scanning. The data from the "NS-1" slices at both the beginning and end of the scanning may be combined with each other to reconstruct an image. An alternative can be provided such that data from the "NS-1" slices at both the beginning and end of the scanning are disregarded, that is, with no relation to imaging, but pulses to excite the "NS-1" slices at both the beginning and end of the scanning are still applied to an object in order to make an MT (magnetization transfer) effect constant.

Alternatively, the multi-slice imaging according to the present embodiment may be configured such that data acquisition from the beginning portion F of the scanning, at which MS-piece slices have yet to be completed, is omitted from the actual excitation and data acquisition. In this case, the actual data acquisition is preferably carried out after an interval of time assigned to the MS-piece slices residing at the beginning of the scanning has passed.

In addition, in the above embodiment, to avoid the explanation from being complicated, the pulse sequence used for multi-slice imaging has been set to a train of pulses based on the FE method (refer to FIG. 3), which is the most fundamental sequence. The pulse sequence, however, may be substituted for a multi-echo type of pulse sequence. If data acquisition is done with multi-echoes, like an EPI (echo planar imaging)-system sequence, a data acquisition time can be shortened by an amount obtained by dividing a matrix size in the phase encode direction by the number of multiple echoes. If the pulse sequence is based on a multiple-echo acquisition technique that uses a plurality of RF pulses, like a fast spin echo method, an offset amount of the carrier frequency of each of all the RF pulses may be changed correspondingly to a moved position of each slice, like the technique shown by the foregoing paper written by AH Herlihy et al.

Second Embodiment

Figure 5:
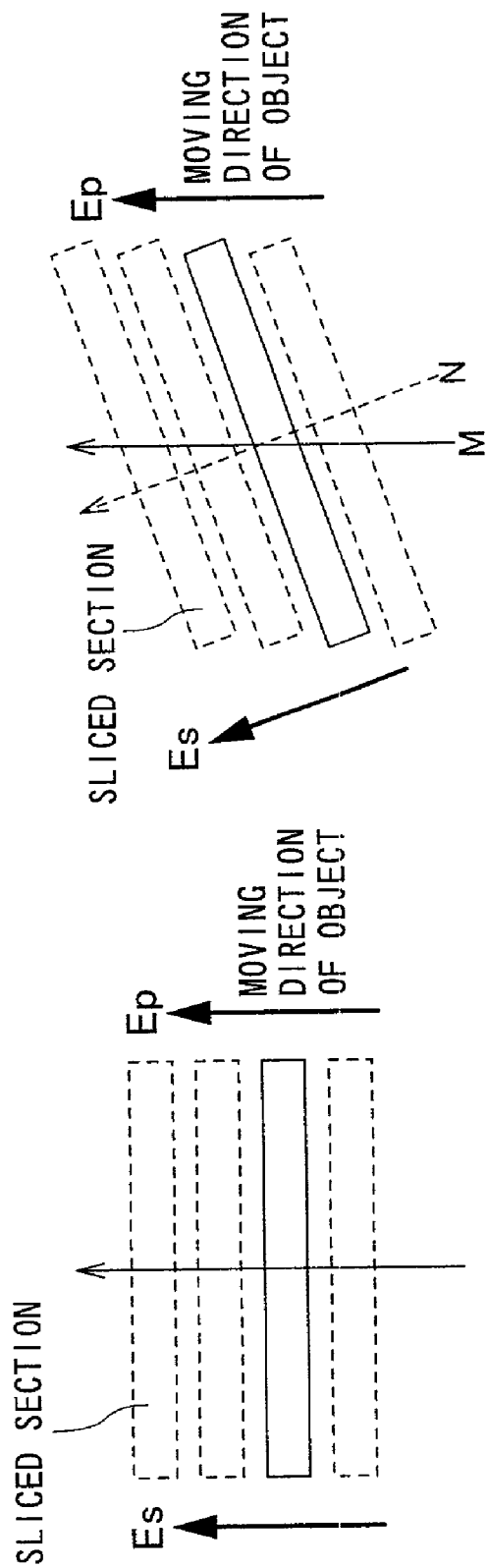
FIG. 5A is an illustration of the positional relationship between a moving direction of an object and a slice selecting direction at an oblique angle=0, comparable to oblique imaging, according to a second embodiment.
FIG. 5B is an illustration of the positional relationship between a moving direction of an object and a slice selecting direction in oblique imaging according to the second embodiment.
Figure 6:
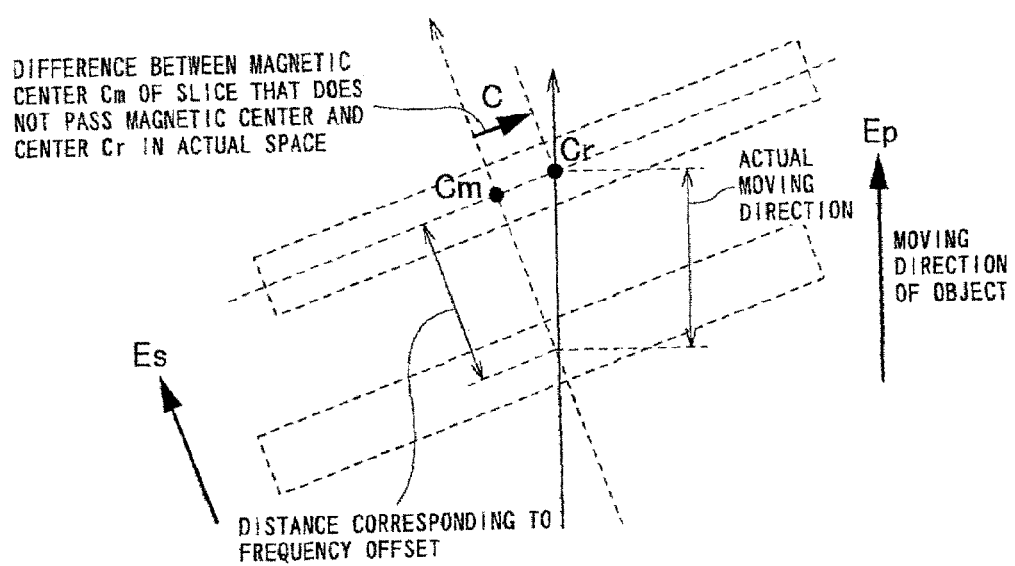
FIG. 6 is a partially enlarged view showing in detail the oblique imaging shown in FIG. 5B.

Referring to FIGS. 5 and 6, a magnetic resonance imaging system according to a second embodiment of the present invention will now be described. The hardware of this system is configured in the same way as that in the first embodiment.

In the foregoing first embodiment, adopted was the configuration in which the moving direction of an object agrees with the slice selecting direction. Instead, the present second embodiment provides an imaging technique called oblique imaging (scan) in which both of the above directions are different from each other. In practical diagnosis, the oblique imaging is performed, for example, in such a manner that a section to be imaged is set along a direction of the OM line of an object (patient).

The oblique imaging according to the present embodiment adopts scanning conditions determined to adjust the carrier frequency for selective excitation in compliance with the geometrical relationship between a moving direction of a patient P and a slice selecting direction.

Practically, as shown in FIG. 5B, the oblique imaging involves both of a moving direction M of an object and a slice selecting direction N. By contrast, as shown in FIG. 5A, both the directions M and N coincide with each other, which is a particular case of the oblique imaging and corresponds to the situation explained in the first embodiment. The relationship between the movement speed V of the tabletop and the offset $\Delta f$ of the carrier frequency, which has been detailed in the first embodiment, can also be described more precisely in terms of a moved speed V' of an object in a slice direction and an offset $\Delta f$ of the carrier frequency. Between V and V', a relationship of V'=V·IE is realized. When a unit vector expressing the moving direction M of the object by Ep and a unit vector expressing the slice selecting direction N by Es, as shown in FIGS. 5A and 5B, an expression of IE=[Ep, Es] showing a scalar product of the unit vectors is provided. Hence, if the product of "V·IE" is newly expressed by V, this newly expressed parameter V can be included into various kinds of imaging parameters. These imaging parameters are determined so as to meet the foregoing conditions before performing the scanning. An offset $\Delta f$ of the carrier frequency, which is also given based on this newly expressed parameter V, is automatically calculated by the host computer or sequencer 5 using the scan conditions given before the scanning. Based on the calculated results, the sequencer 5 commands the transmitter 8T to output a carrier wave having a frequency of "central frequency $f_0$+offset frequency $\Delta f$."

Determining the offset $\Delta f$ of the carrier frequency in this way allows the positions of the oblique multiple slices to automatically track a movement of an object P. In consequence, the same oblique slices to the object can be selective-excited at any time.

By the way, as shown in FIG. 6, for a slice that does not pass the magnetic center of the static field produced by the magnet 1, there is left a difference between a magnetic center Cm of the slice and a center Cr in the actual space. In cases where an object is stationary which is ordinary imaging, such a difference caused during the data acquisition becomes constant, just resulting in that the center of a reconstructed image is moved to the "magnetic center Cm." That is, there is less influence on imaging. Additionally, the technique disclosed by U.S. Pat. No. 5,084,818 can be used, if necessary, to correct such influence.

Unlike the above ordinary imaging, the present embodiment provides a different situation in that contradictory data acquisition is carried out every phase encode, due to the fact that an object is moved. Thus, the correction of phases is necessarily required. The calculator 10 of the present embodiment is therefore configured such that it corrects the phases in the following manner. The calculator 10 serves, therefore, as phase correcting means and reconstructing means, which compose part of the constituents of the present invention.

This phase correction is an adjustment operation that makes the spin phases zero at the central position Cr of a slice in the actual space. As shown in FIG. 6, a vector C directing from the magnetic center Cm to the center Cr in the actual space can be defined. This vector C is included in a plane in which there are both of a unit vector Ee in a phase encode direction and a unit vector Er in a readout direction. When phase encode amounts given by gradients are K=(kr, ke) in the k-space, their phases at the center Cr in the actual space can be expressed by $$\exp(2\pi i [K, C]).$$

Thus, the phases can be corrected by multiplying acquired data by $$\exp(-2\pi i [K, C]).$$

This phase correction makes it possible that even when the oblique imaging is performed while an object is moved, MR signals can securely be acquired with no phase contradiction which has been caused from the fact that the object itself is moved. Accordingly, the data of which spin phases are mapped in order can be used to obtain high-quality MR images through ordinary image-reconstruction processing.

Other Embodiments

The foregoing multi-slice imaging and oblique imaging according to the first and second embodiments can be modified as described below:

(First Modification)

Figure 7A:
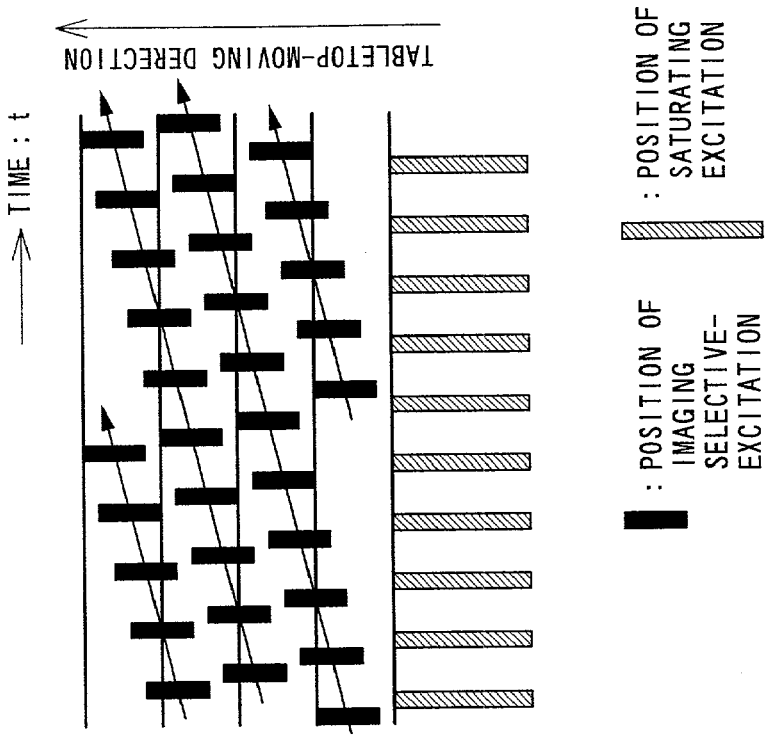
FIG. 7A exemplifies pulse-applied positions in imaging with a pre-saturation pulse, which is carried out according to one modification.
Figure 7B:
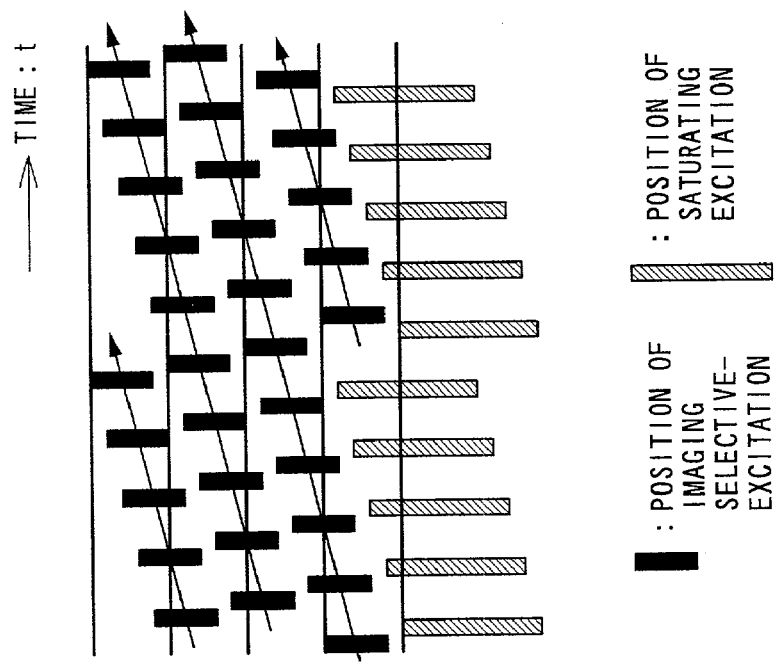
FIG. 7B exemplifies pulse-applied positions in imaging with a pre-saturation pulse, which is carried out according to another modification.

The foregoing multi-slice imaging and oblique imaging are able to additionally employ a variety of preparation pulses. FIGS. 7A and 7B explain multi-slice imaging, respectively, in which a pre-saturation pulse is applied as a preparation pulse every time each of three multi-slices is selectively excited one time. The information indicating this pre-saturation pulse is incorporated into a pulse sequence in advance. The sequencer 5 that has accepted the pulse sequence information drives both the transmitter 8T and the gradient power supply 4 in compliance with the pre-saturation pulse information, so that the pre-saturation pulse is applied to an object. The pre-saturation pulse is required that it be applied to a position considerably close to a current-scanned slice. In order to cope with this, as shown in FIG. 7A, an applied position of the pre-saturation pulse is changed in compliance with a moved distance of an object.

On the other hand, characteristics required for the preparation pulse depend on what type of object is given. In cases where there is no particular request for applying the pre-saturation region to positions considerably close to multi-slices undergoing a main scan, the pre-saturation pulse can be applied as depicted in FIG. 7B. That is, pre-saturated regions are fixed at predetermined positions far from any slice by a certain distance capable of preferably avoiding magnetic interference, regardless of movements of the multi-slices.

(Second Modification)

A second modification relates to use of gradient moment nulling (GMN) for compensating disturbances in the phases of MR signals. Such disturbances are caused due to motions of an object. In the field of MRI, the gradient moment nulling is also referred to as rephasing, flow rephasing, flow compensation, or others.

In the state where the tabletop is moved at a constant speed, thereby an object on the tabletop being also moved at that speed, it is considered that the whole object is subject to the influence of the first order moment (i.e., velocity moment) due to the movement. To remove this influence, phase compensating pulses for the first order or the second or more order gradient moment nulling are incorporated in the slice gradient of the pulse sequence used in the first or second embodiment. The slice gradient is applied in a moving direction of the object. For oblique imaging, such gradient moment nulling pulses may be incorporated into the readout gradient and/or phase encode directions.

Accordingly, even if an object is moved at a constant speed during scanning, no disturbance will be caused in signal phases. Artifacts attributable for such phase disturbances are therefore prevented from being generated, thereby higher-quality MR images being provided.

(Third Modification)

The foregoing gradient moment nulling technique requires an additional application of the phase compensation pulses. Hence this technique is not always usable, because an application time of the gradients becomes longer.

This inconvenient situation can be improved, in that case that each pulse sequence used for imaging in the first and second embodiments is composed of a fast SE method that uses RF refocusing pulses. Specifically, a modification configured to meet a VIPS (Velocity Independent Phase-shift Stabilization) technique adopted in an object's moving direction can be provided.

The VIPS technique, which is for example taught by the paper "Proc. Intl. Soc. Magn. Reson. Med. the seventh meeting (1999), p. 1910," is imaging ruled in terms of spin phases that describe behaviors of spin echoes created by a pulse sequence based on, for example, the fast SE method. This VIPS technique can be summarized as an imaging technique that satisfies a "Ø/2 condition."

Employing the VIPS technique eliminates the necessity of additionally using the phase compensating pulse, such as gradient moment nulling pulses. Hence, with high data acquisition efficiency still maintained, it is possible to perform the foregoing multi-slice imaging or oblique imaging, thus the foregoing various advantages being provided.

As described above, the magnetic resonance imaging system of the embodiments allows imaging techniques and image-quality improving techniques, which are truly helpful in actual medical treatment, to be used also for imaging that involves a continuous movement of an object. Such techniques include the multi-slice imaging (including the oblique imaging of multiple slices) and the method of reducing artifacts caused due to motions of an object. Accordingly, the moving imaging technique can be enhanced. In addition, even if the MRI system provides only a narrow imaging range (i.e., narrow photographable range), a region of which range is wider than the narrow imaging range can be imaged at a higher speed, so that a patient's throughput can be improved.

The present invention may not be limited to the foregoing embodiments, and may be embodied in other specific forms without departing from the spirit or essential characteristics thereof.

What is claimed is:

1. A magnetic resonance imaging system comprising:
   image range providing means for providing a spatially-fixed imaging spatial range in which three or more regions of an object to be imaged are spatially selected in a predetermined moving direction along which the object is moved;
   moving means for continuously moving the object along the predetermined moving direction so that spatial positions of the three or more regions are continuously moved through the imaging spatial range along the moving direction;
   exciting means for space-selectively and magnetically exciting the three or more regions of the object that is in motion so that each region is repeatedly excited a plurality of times in the imaging spatial range at first intervals, of time during each of which two or more remaining regions are in turn excited at second intervals of time shorter than the first intervals of time;
   position-moving means for moving spatial positions of the three or more regions so as synchronously track a movement of the object in the moving direction;
   acquiring means for acquiring echo data from the three or more excited regions of the object while the object is continuously moved by the moving means; and
   processing means for processing the acquired echo data to produce image data from the echo data.

2. A method for magnetic resonance imaging, which provides a spatially-fixed imaging spatial range in which three or more regions of an object to be imaged are spatially selected in a predetermined moving direction along which the object is moved continuously, spatial positions of the three or more regions being continuously moved through the imaging spatial range along the moving direction, the method comprising:
   space-selectively and magnetically exciting the three or more regions of the object while the object is moved, each region being repeatedly excited a plurality of times in the imaging spatial range at first intervals of time during each of which two or more remaining regions are in turn excited at second intervals of time shorter than the first intervals of time, spatial positions of the three or more regions being moved so as to synchronously track a movement of the object in the moving direction;
   acquiring echo data from the three or more excited regions of the object; and
   producing image data from the acquired echo data.

3. A magnetic resonance imaging method as in claim 2, wherein the three or more regions are multi-slices of the object.

4. A magnetic resonance imaging method as in claim 3, wherein the multi-slices have a slice-selective axis direction corresponding to the moving direction of the object.

5. A magnetic resonance imaging method as in claim 3, wherein the multi-slices have a slice-selective axis direction that is different from the moving direction of the object.

6. A magnetic resonance imaging method as in claim 3, wherein the step of exciting includes adding another slice to a tail of the multi-slices as a slice belonging to the three or more multi-slices in the moving direction, in cases where a head slice of the multi-slices in the moving direction goes beyond the imaging spatial range.

7. A magnetic resonance imaging system comprising:
   a image range providing unit providing a spatially-fixed imaging spatial range in which three or more regions of an object to be imaged are spatially selected in a predetermined moving direction along which the object is moved;
   a moving unit, which includes a couch on which the object is laid, driving the couch so that spatial positions of the three or more regions are continuously moved through the imaging spatial range along the moving direction;
   a controller configured to space-selectively and magnetically excite the three or more regions of the object so that each region is repeatedly excited a plurality of times in the imaging spatial range at first intervals of time during each of which two or more remaining regions are in turn excited at second intervals of time shorter than the first intervals of time and also move spatial positions of the three or more excited regions so as to synchronously track a movement of the object in the moving direction;
   a receiver configured to echo data from the three or more excited regions of the object; and
   a reconstruction unit configured to produce image data from the acquired echo data.

8. A magnetic resonance imaging system as in claim 7, wherein the plurality of regions are multi-slices of the object.

9. A magnetic resonance imaging system as in claim 8, wherein the multi-slices have a slice-selective axis direction agreeing with the moving direction of the object.

10. A magnetic resonance imaging system as in claim 8, wherein the multi-slices have a slice-selective axis direction that is different from the moving direction of the object.

11. A magnetic resonance imaging system as in claim 8, wherein the controller includes means for adding another slice to a tail of the multi-slices as a slice belonging to the three or more multi-slices in the moving direction, in cases where a head slice of the multi-slices in the moving direction goes beyond the imaging spatial range.

12. A magnetic resonance imaging system comprising:
   an image range providing unit providing a spatially-fixed imaging spatial range in which three or more regions of an object to be imaged are spatially selected in a predetermined moving direction along which the object is moved;

a moving unit continuously moving the object along the predetermined moving direction so that spatial positions of the three or more regions are continuously moved through the imaging spatial range along the moving direction;

an exciting unit space-selectively and magnetically exciting the three or more regions of the object that is in motion so that each region is repeatedly excited a plurality of times in the imaging spatial range at first intervals of time during each of which two or more remaining regions are in turn excited at second intervals of time shorter than the first intervals of time;

a position-moving unit moving spatial positions of the three or more regions so as to synchronously track a movement of the object in the moving direction;

an acquiring unit acquiring echo data form the three or more excited regions of the object while the object is continuously moved by the moving unit; and a processing unit processing the acquired echo data to produce image data from the echo data.

13. A magnetic resonance imaging system as in claim 12, wherein the position-moving unit is equipped with a couch with a tabletop on which the object is laid, the couch having a mechanism for moving the tabletop in a longitudinal direction of the tabletop corresponding to the moving direction.

14. The magnetic resonance imaging system as in claim 12, wherein the plurality of regions are multi-slices of the object.

15. A magnetic resonance imaging system as in claim 14, wherein the multi-slices have a slice-selective axis direction agreeing with the moving direction of the object on the couch.

16. A magnetic resonance imaging system as in claim 14, wherein the multi-slices have a slice-selective axis direction that is different from the moving direction of the object on the couch.

17. A magnetic resonance imaging system as in claim 16, wherein the position-moving unit is configured to change the carrier frequency of the selective-excitation RF pulse in compliance with a geometrical relationship between the moving direction of the object and the slice selecting direction.

18. A magnetic resonance imaging system as in claim 16, wherein the acquiring unit is configured to acquire the echo data from the selectively excited slices, and the processing unit includes phase correcting means for correcting a phase of echo data acquired by the acquiring unit on the basis of a geometrical relationship between a position of the object and a direction in which a gradient is applied, and reconstructing unit for reconstructing the echo data of which phases are corrected by the phase correcting unit.

19. A magnetic resonance imaging system as in claim 14, wherein the exciting unit is provided with means for adding another slice to a tail of the multi-slices as a slice belonging to the three or more multi-slices in the moving direction in cases when a head slice of the multi-slices in the moving direction goes beyond the imaging spatial range.

20. A magnetic resonance imaging system as in claim 14, wherein the position-moving unit is configured to change slice by slice a carrier frequency of a selective-excitation RF pulse to be applied to the multi-slices.

21. The magnetic resonance imaging system as claim 12, wherein the exciting unit includes means for selectively exciting in sequence the three or more regions by using a preparation pulse whose position applied to the object is moved in response to the movement of the three or more regions.

22. A magnetic resonance imaging system as in claim 12, wherein the exciting unit includes means for selectively exciting in sequence the three or more regions by use of a pulse sequence having a gradient pulse to be applied in the moving direction of the object, in which a phase compensation pulse for nulling a gradient moment of a first or second order is added to at least part f the gradient pulse.

23. A magnetic resonance imaging system as in claim 12, wherein the exciting unit includes means for selectively exciting in sequence the three or more regions by use of a pulse sequence, formed based on a fast spin echo technique, including a gradient that meets, at least partly a VIPS condition.

* * * * *